(12) United States Patent
Asundi et al.

(10) Patent No.: US 7,477,362 B2
(45) Date of Patent: Jan. 13, 2009

(54) MOIRÉ INTERFEROMETRIC STRAIN SENSOR

(75) Inventors: Anand Krishna Asundi, Singapore (SG); Anish Priyadarshi, Singapore (SG); Subodh Gautam Mhaisalkar, Singapore (SG)

(73) Assignee: Nanyang Technological University, Singapore (SG)

( * ) Notice: Subject to any disclaimer, the term of this patent is extended or adjusted under 35 U.S.C. 154(b) by 183 days.

(21) Appl. No.: 11/235,077

(22) Filed: Sep. 27, 2005

(65) Prior Publication Data

US 2007/0070327 A1    Mar. 29, 2007

(51) Int. Cl.
G01L 1/24  (2006.01)
G01B 9/02  (2006.01)
G01D 5/36  (2006.01)

(52) U.S. Cl. .................. 356/35.5; 356/521; 250/237 G
(58) Field of Classification Search .................. 356/32, 356/35.5, 521; 250/237 G
See application file for complete search history.

(56) References Cited

U.S. PATENT DOCUMENTS

| | | | | | |
|---|---|---|---|---|---|
| 4,432,239 | A | * | 2/1984 | Bykov | 73/800 |
| 5,026,154 | A | * | 6/1991 | Deason | 356/35.5 |
| 5,233,174 | A | * | 8/1993 | Zmek | 250/201.9 |
| 5,737,075 | A | * | 4/1998 | Koch et al. | 356/310 |
| 5,828,455 | A | * | 10/1998 | Smith et al. | 356/515 |
| 5,898,486 | A | * | 4/1999 | Chesko et al. | 356/35.5 |
| 6,587,211 | B1 | * | 7/2003 | Gelbart | 356/499 |
| 7,170,597 | B1 | * | 1/2007 | Hooper et al. | 356/317 |

OTHER PUBLICATIONS

Asundi et al., Opt. Eng., vol. 39, No. 6, pp. 1645-1651 (Jun. 2000).

* cited by examiner

*Primary Examiner*—Patrick J Connolly
(74) *Attorney, Agent, or Firm*—Birch, Stewart, Kolasch & Birch, LLP

(57) ABSTRACT

A moiré interferometric strain sensor for detecting strain on a specimen, a diffraction grating being on the specimen, the strain sensor including an array of a plurality of microlenses for receiving at least one reflected beam of at least one incident beam upon the specimen; and a detector array at a focal plane of the array of a plurality of microlenses.

39 Claims, 7 Drawing Sheets

MOIRÉ INTERFEROMETRIC STRAIN SENSOR

FIELD OF THE INVENTION

This invention relates to a moiré interferometric strain sensor and refers particularly, through not exclusively, to such a sensor using multiple microlenses.

BACKGROUND OF THE INVENTION

Strain measurement is important in mechanics, material science and engineering. Devices used for strain measurement include mechanical extensometers and electrical resistance strain gauges. Optical devices such as moiré, speckle and holography have recently been developed and may also be used. Optical devices are whole-field, non-contact and sensitive methods for static and dynamic strain measurement. However, most optical devices provide contours of displacement components which need to be processed to obtain the distribution of strain and stress. For example, moiré interferometry uses a high frequency (typically 1200 lines/mm) diffraction grating replicated onto the specimen to map the whole field deformation in two perpendicular directions. The technique was extended to micron-level spatial resolution capability using a fiber optic based Micro-Moiré Interferometer (MMI). Numerical and optical schemes have been proposed to provide strain indications from these deformation maps.

However, the ubiquitous electrical resistance strain gauge is still popular since they can directly measure strain at a specific point.

Optical diffraction principles were proposed as an alternative by directly determining strain using a shift of a diffracted beam. Such Optical Diffraction Strain Sensors (ODSS) avoid the difficulty in fringe pattern interpretation associated with most optical techniques. With the advent of sensitive Position Sensing Detectors (PSD), the capabilities of the ODSS rival that of an electrical resistance strain gauge. However, as with the electrical strain gauge, the ODSS is still a point measurement scheme. Therefore, it has not been able to compete with the well-established electrical strain gauge.

In the paper "Optical Strain Sensor Using Position-Sensitive Detector and Diffraction Grating: Error Analysis" by Asundi and Zhao (Opt. Eng. 39(6) June 2000 at pages 1645 to 1651), the contents of which are hereby incorporated in their entirety as if disclosed herein, there is disclosed a strain sensor having a single incident light beam, and two detectors that is also able to detect strain at a single point only.

To have multi channel strain sensor where strains can be simultaneously and directly measured at many points requires a myriad of wires and data acquisition systems.

SUMMARY OF THE INVENTION

In accordance with a first preferred aspect there is provided a moiré interferometric strain sensor for detecting strain on a specimen, the strain sensor comprising:
  (a) an array of a plurality of microlenses for receiving at least one diffracted beam of at least one incident beam upon the specimen; and
  (b) an array of a plurality of detectors at a focal plane of the array of a plurality of microlenses.

According to a second preferred aspect there is provided a method for detecting a strain on a specimen, the method comprising placing a high frequency diffraction grating on the specimen; providing at least one incident beam on the specimen at the diffraction grating to cause at least one diffracted beam; using an array of a plurality of microlenses to receiving the at least one diffracted beam; and detecting the at least one diffracted beam at an array of a plurality of detectors at a focal plane of the array of a plurality of microlenses.

According to a third preferred aspect there is provided a moiré interferometric strain sensor for detecting strain on a specimen, a diffraction grating being on the specimen, and at least one light source for directing at least two light beams on the diffraction grating, the at least two light beams being able to illuminate at least a major portion of the diffraction grating without movement of the at least two light beams.

According to a fourth preferred aspect there is provided a method for detecting a strain on a specimen, the method comprising placing a high frequency diffraction grating on a surface of the specimen; providing at least one light source for directing at least two light beams on the diffraction grating, the at least two light beams illuminating at least a major portion of the diffraction grating without movement of the at least two light beams.

The at least two light beams may be coincident on the diffraction grating when the diffraction grating is in a reference state. The at least two light beams may be symmetrical about a line perpendicular to the specimen. The at least two light beams may be of the same frequency. The angle of symmetry may be determined by the diffraction grating frequency and the frequency of the at least two light beams. There may be a single light source, the at least two beams being from the single light source. The at least two beams may be collimated beams.

The array of a plurality of microlenses may be close packed or spaced apart. The detectors may be a charge coupled device or a complimentary metal oxide device.

There may be a single microlens for each of the plurality of detectors; and the microlens array may comprise a plurality of microlenses all being substantially identical.

There may be at least one further array of microlenses, the at least one further array of microlenses being of a different or similar sensitivity to that of the array of microlenses.

The microlens array may be a virtual microlens array and may be produced by a spatial light modulator. The spatial light modulator may be a liquid crystal display, a liquid crystal on silicon, or a digital micro-mirror device.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

This embodiments described provide a method and apparatus able to measure strain simultaneously at multiple points using optical diffraction techniques.

Figure 1:
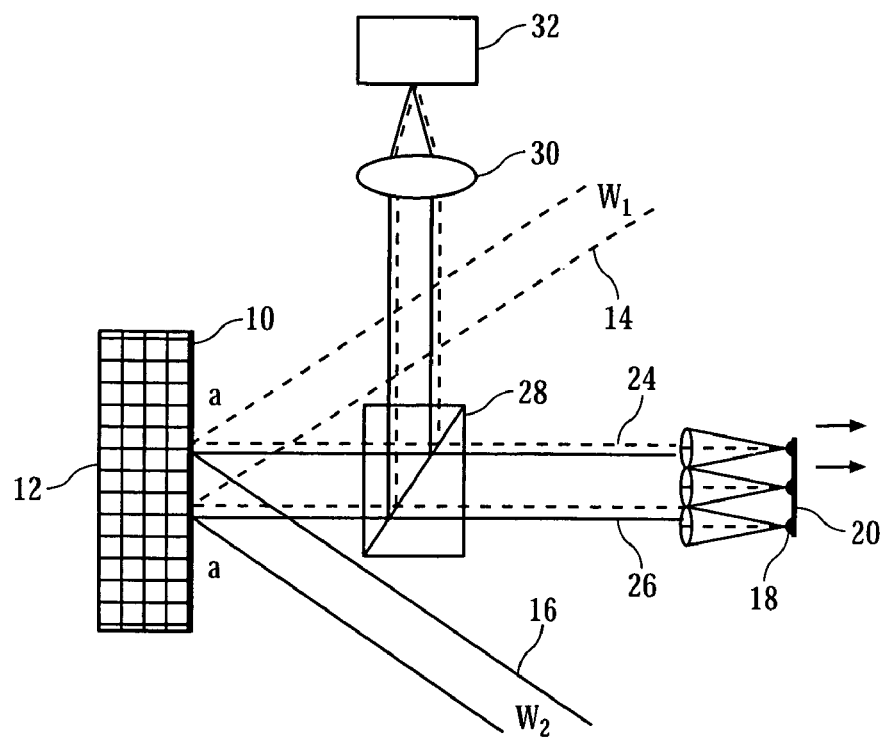
FIG. 1 is an illustration of an optical scheme for a first preferred embodiment of an Integrated Moiré Inteferometric Strain Sensor.
Figure 2A:
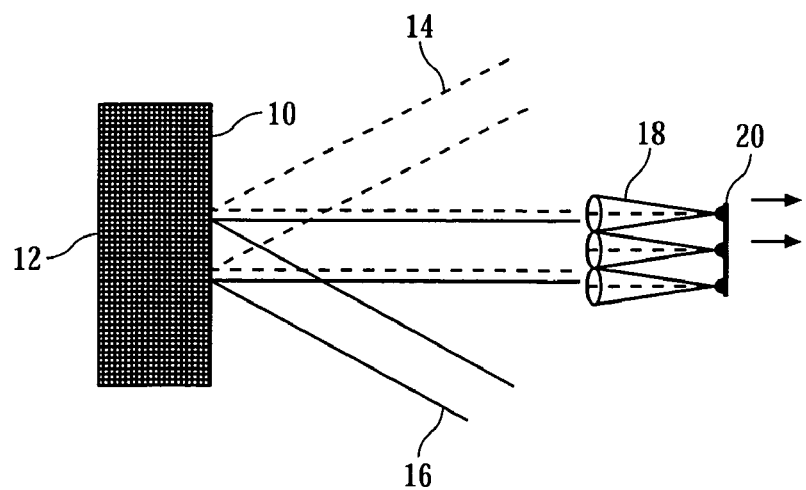
FIG. 2 is an Illustration showing the effect of specimen grating deformation on the displacements of focused spots with respect to each other from the lens array:
  (a) for an initial no-deformation specimen; and
  (b) for a deformed specimen.
Figure 2B:
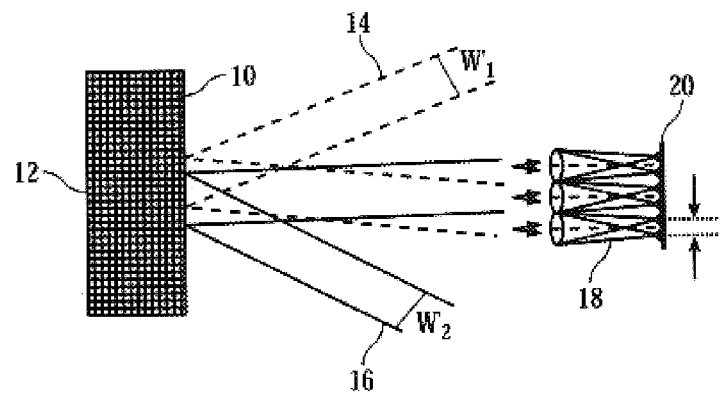
Figure 9:
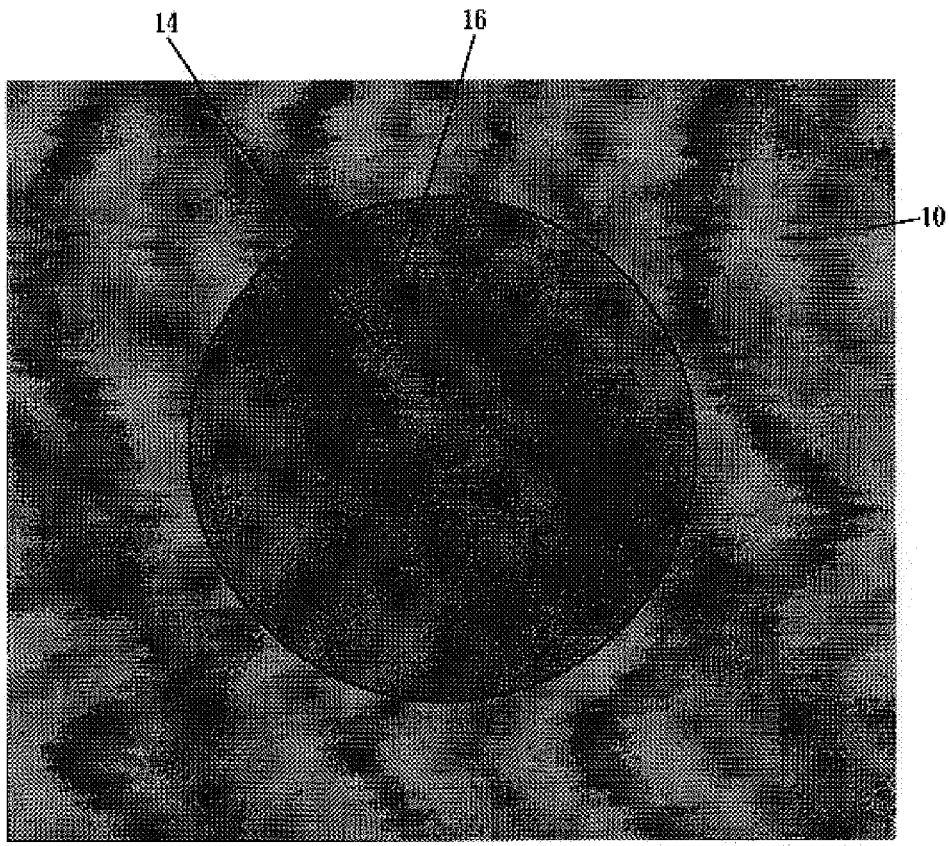
FIG. 9 is an illustration of the incidence of light onto the diffraction grating.

As shown in FIGS. 1, 2 and 9 a high frequency grating 10 is attached to the surface of a specimen 12. The grating frequency determines the sensitivity. The specimen 12 is illuminated by two light beams 14, 16 each at a prescribed angle a determined by the frequency of the grating 10. The laser wavelengths W1 and W2 have some control on sensitivity.

Figure 4A:
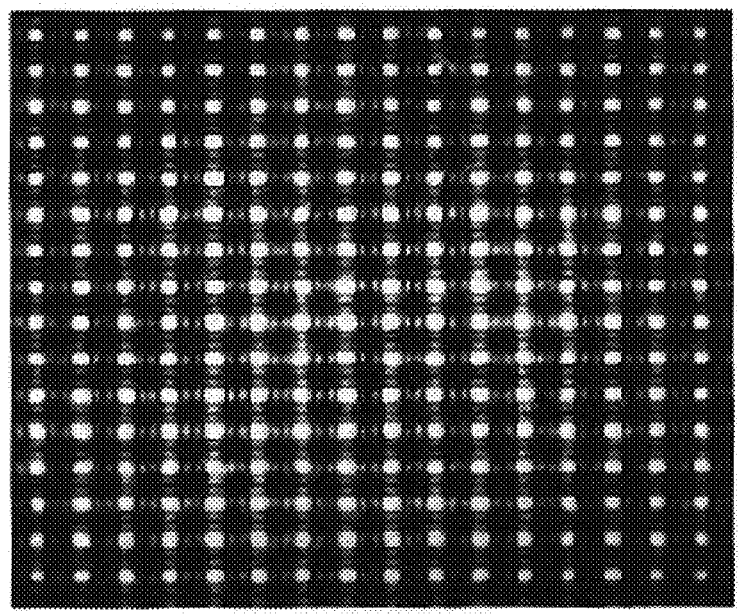
FIG. 4 shows:
  (a) spots image captured by microlens arrays; and
  (b) null field fringes by detector array.
Figure 4B:
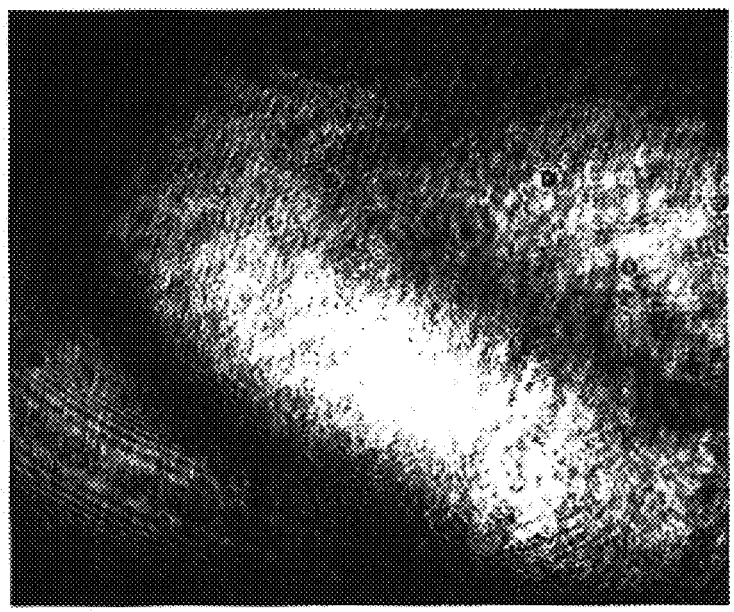

Each beam 14, 16 is diffracted by the specimen 12 and is separately sampled using a microlens array 18 placed in front of a detector array 20. The microlens array 18 comprises a plurality of microlenses 19. Each detector in the array 20 may be a Charged Coupled Device (CCD), complimentary metal oxide (CMOS) or other multi-point position sensor detector (PSD). The detector array 20 is placed at the focal plane of microlens array 18; there being one detector array 20 for each microlens array 18. A spot from each of the microlenses 19 is formed on the detector array 20, there being one spot for each of the illuminating beams thus giving two spots for each microlens 19 and detector 20. (FIG. 4 and FIG. 5). Separation of the spot centroids of the two beams for each microlens 19 is measured by known image processing methods. As shown on FIG. 2, the separation is directly proportional to the normal (or shear) strain component that is the direction perpendicular to the grating lines at the corresponding positions on the specimen 12 as detected by the microlens array 18.

It is preferred for both the beams 14, 16 to illuminate the entire area under scrutiny. This may be all or a major portion of the grating 10, as shown in FIG. 9. In this way strain in the area under scrutiny can be quickly determined without movement of the beams 14, 16. As such the beams 14, 16 can be focused on the one location, and do not require the ability to move. This may be of considerable advantage when dealing with relative small objects, such as during the manufacture of MEMS devices. Furthermore, it is of advantage for the two beams 14,16 to be coincident when the grating 10 is not under strain—the reference state—as shown in FIG. 9. The beams 14, 16 are shown on FIG. 1 and FIG. 2(a) as being not co-incident. This is solely for the purpose of illustration as the two beams 14, 16 are co-incident. The shape of the incident area of the beams 14, 16 on the diffraction grating 10 will depend on the angle of incidence of the beams 14, 16. If the angle is 90 degrees, the shape will be circular, as shown. The more the angle varies from 90 degrees, the more elliptical the shape will become.

At the same time, Moiré Interferometric (MI) fringes may be recorded using the traditional Moiré imaging system comprising a beam splitter 28, an objective lens 30 and a detector array 32.

The system can simultaneously record contours of displacement components in the direction perpendicular to the grating lines by interference of the two beams reflected by the specimen 12 and diffracted by the grating 10. The result is shown on FIGS. 4 and 5.

Two symmetrical beams 14, 16 are used. The two beams 14, 16 should be symmetrical about a line perpendicular to the surface of the specimen 12. The angle of symmetry is determined by the frequency of the grating and the wavelength of the source of the beams 14, 16. It is preferred that the beams 14, 16 are of the same frequency and more preferably are from the same source. That source may be a laser. Each beam 14, 16 may comprise more than one beam. As shown on FIG. 1, each beam comprises a collimated beam. A collimated beam has the advantage of a flat wavefront. As shown on FIG. 9, the angle of symmetry is quite small as the beams are incident on the diffraction grating 10 with a substantially circular shape. The greater the angle of symmetry, the more elliptical the shape will be.

The beams 14, 16 are directed towards the specimen 12 with the grating 10 and are diffracted by the specimen 12, onto which is bonded the grating 10, and captured by the microlens array 18. The bonding may be by any suitable bonding method or apparatus. The diffracted beams 24, 26 respectively emerge as distorted wavefronts. The wavefront shape at the plane of the microlens 18 array is identical to the shape at the plane of the grating 10. The microlens array 18 forms the array of spot images on the detector array 20 as shown in FIGS. 3 and 4.

FIG. 4 illustrates the usual approach to determine the wavefront shape from the detector array spots image formed by the microlens array 18. Without loss of generality, a small point on the diffraction grating is considered. Two rays illuminate this point along the ±α directions, where a is given by $$\sin \alpha = \lambda f \quad (1)$$

where $\lambda$ is the wavelength of the laser used and f is the frequency of the grating. From the diffraction equation $$\sin \beta = m\lambda f + \sin \alpha \quad (2)$$

where $\beta$ is the angle of the diffracted beam with respect to the surface normal and m is the diffraction order, it is observed that the +1 order of beam incident at an angle $-\alpha$, emerges normal to the grating plane ($\beta=0$) as does the $-1$ order of the $+\alpha$ beam. When the specimen deforms, i.e. the pitch of the grating changes to $f+\Delta f$, equation (2) becomes $$\sin(\beta+\Delta\beta) = \mp \lambda(f+\Delta f) + \sin \alpha \quad (3)$$

where m =1, and $\Delta\beta$ is the change in the diffraction angle.

From this the following relation between change in frequency and change in diffraction angle can be derived $$\pm\Delta\beta = \lambda\Delta f \quad (4)$$

The derivative of displacement (strain) in the direction perpendicular to the grating line is proportional to the change in pitch or frequency of the grating. Thus $$\varepsilon = \frac{\Delta f}{f} \quad (5)$$

$$= \frac{\Delta \beta}{\lambda f}$$

Using matrix optics formulation, the matrix equation for a parallel beam passing through a lens followed by propagation by one focal length, can be written as $$\begin{bmatrix} x_{out} \\ \theta \end{bmatrix} = \begin{bmatrix} 0 & F \\ \frac{-1}{F} & 1 \end{bmatrix} \begin{bmatrix} x_{in} \\ \beta \end{bmatrix} \quad (6)$$

where $x_{out}$ and $\theta$ are the position and slope of the rays at the output (focal plane of lens), $x_{in}$ and $\beta$ are the ray position and angle at the input (grating) plane and F is the focal length of the lens. For the undeformed case it is observed that $x_{out}$ is zero for both diffracted rays as they emerge parallel to the optical axis. If the specimen and hence the specimen grating were tilted, then once again both rays are coincident but since the angle $\beta$ is non-zero, the spots are not at the optical axis ($x_{out}$ is not zero). When the specimen deforms, $\beta$ changes locally based on strain as per equation (5) and hence $x_{out}=F\beta$.

A single illumination beam 14 or 16 may suffice. However, it is noted from equation (6) that a rigid body tilt of the specimen grating 10, would also cause $\beta$ to change and hence $x_{out}$ would also change. For two symmetrical illuminating beams 14, 16, rigid body tilt would still cause a change in $x_{out}$ but it will same for the two beams 14, 16 and thus the spots will move by the same amount in the same direction. A change in the frequency of the grating 10 due to strain would cause the two beams 14, 16 to diffract in equal but opposite directions. Hence the diffraction spots move in different directions and hence can be measured.

In this system each microlens 19 samples a specific part of wavefront emerging from the grating, i.e. the diffracted ray emerging from a specific portion of the grating. The size of the microlens 19 determines the area sampled and hence is related to the gauge length of the strain sensor. In the undeformed case the spots from the two illumination rays overlap, while when the specimen deforms, the diffracted dots separate either in the horizontal or the vertical directions. The relative separation (p) between the two spots gives the derivative of displacement, i.e. strain from equations (5) and (6) as $$\varepsilon = \frac{p}{2F\lambda f} \quad (7)$$

The factor of 2 in the denominator is due to the fact that the two spots moved in opposite directions.

Demonstration of this new method is shown using a 1200 lines/mm grating 10 on a glass substrate as the specimen 12. The grating 10 was mounted on a stage that could be translated as well as rotated in a plane. The microlens array 18 was placed 12 cm from the plane of the grating 10 to capture the sampled spots image.

Figure 5A:
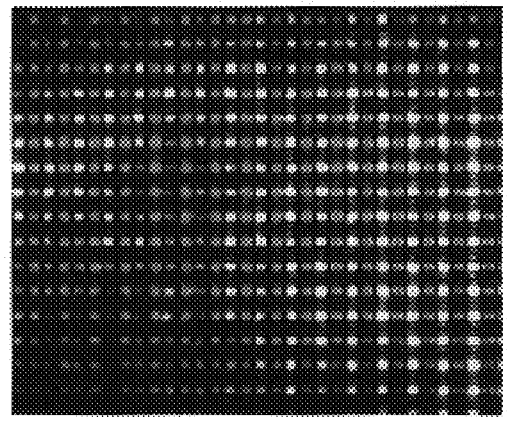
FIG. 5 shows final spots images: the two colours correspond to spot images from the two illuminating beams:
  (a) due to change in frequency (extensional strain);
  (b) due to change in angle (rotational/shear strain);
  (c) Moiré interferometric fringe pattern due to change in frequency; and
  (d) Moiré interferometric fringe pattern due to change in angle.
Figure 5B:
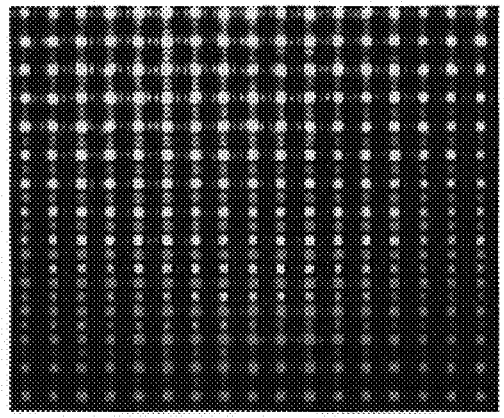
Figure 5C:
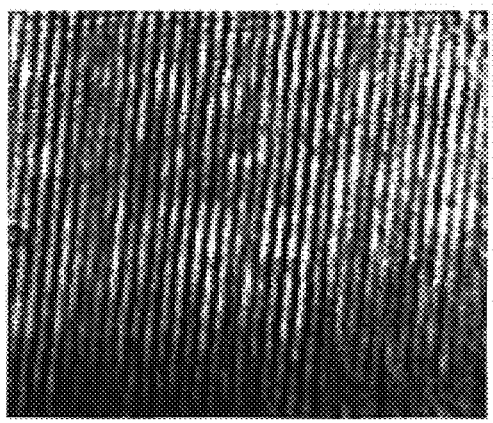
Figure 5D:
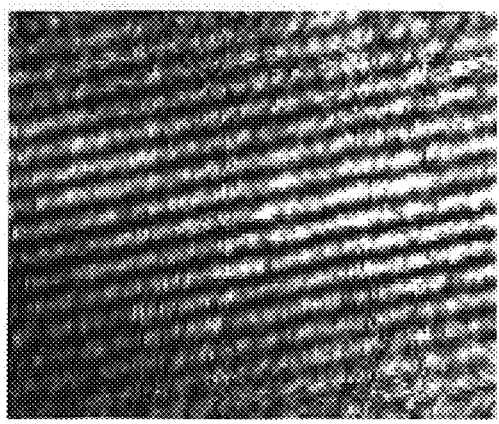

The null field was established by overlapping the spots from both the diffracted wavefronts (FIG. 5a). The corresponding fringe pattern, referred to as the null field, was also recorded as shown in FIG. 5b. Two types of fictitious deformations were accorded to the specimen. In the first case, the grating was rotated in its plane simulating a shearing type strain. In the second case the angle of incidence of one of the beams was changed. This simulates a change in frequency along the direction of the grating lines, thus simulating normal strain.

The spots image and fringe pattern for the deformed state are shown in FIG. 5. Since in this case, the gradient of deformation is constant over the whole-field, all the spots are separated by the same amount. For the case of rotation, the spots move in the vertical direction, while for the normal strain the spots move in the horizontal plane. Hence one can separate the normal and shearing components of the strain.

The spot centroids were determined by capturing the spots image for the reference state of the object. The image is segmented into zones based on the configuration of the microlens array 20. The centroids in each segment are then calculated. The same process is followed for the second beam. The deformed image is followed and the same procedure followed. The spot separation is then determined. The strain can be determined by using the position of the dots from the reference and deformed images. Using the system parameters, equation. (7) becomes $\varepsilon=0.082$ (p). The camera has a pixel size of 8.6 μm (H)×8.3 μm (V) and hence the strain sensitivity is $0.71*10^{-3}$ and $0.69*10^{-3}$ per pixel shift in the horizontal and vertical direction respectively. Using sub-pixel centroid detection algorithms, the sensitivity can be significantly improved.

From the spots image and the fringe patterns shown in FIG. 5, the calculated derivative of displacements agree favorably as shown in the table below.

TABLE

| Deformation | Pixel Shift from arrayed lens Camera (pixels) Pixel size 8.6 μm × 8.3 μm | $\varepsilon = \frac{p}{2F\lambda f}$ | MI Fringe spacing (Pixels) Pixel size 11 μm × 11 μm | $\varepsilon = \frac{1}{2400 * \text{fringespacing}}$ |
|---|---|---|---|---|
| Extension | 9 | 0.0064 | 5 | 0.0075 |
| Rotation | 7 | 0.0048 | 7 | 0.0054 |

For the spot image the derivative of displacement was calculated using the strain sensitivity multiplied by the pixel number, while for the moiré interferometric the derivative of displacement is given as the reciprocal of the fringe spacing multiplied by the frequency of the reference grating which is twice that of the specimen grating.

The strain gauge is able to determine the in-plane strain and/or geometric changes at multiple point of the specimen, and is effective for diverse engineering materials, and diverse applications, particularly for composites such as in the study of strain concentration, crack initiation, residual strain and the micro/macro mechanics of composite structures.

Figure 3A:
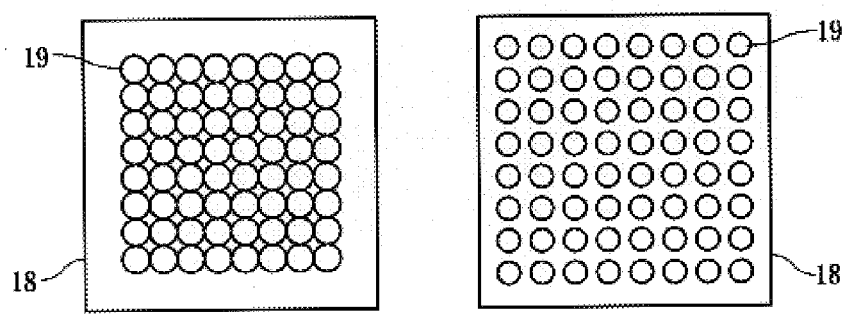
FIG. 3(a) is an illustration of two preferred mircolens arrays.

Different microlens arrays 18 of different materials and various array dimensions and focal length may be used. As shown in FIG. 3(a) they may be closely packed or spaced apart. The size of the microlenses 19 may be 144 μm with a focal length of 8 mm. The microlenses 19 should all be substantially the same.

As shown in FIG. 3(a) the microlens arrays 18 are both regular and symmetrical—both have an 8×8 configuration. This is 8 lenses wide and 8 lenses high. The number of microlenses 19 the array 18 uses will depend on the nature of the strain sensor required, and the size and nature of the specimen 12.

Figure 3B:
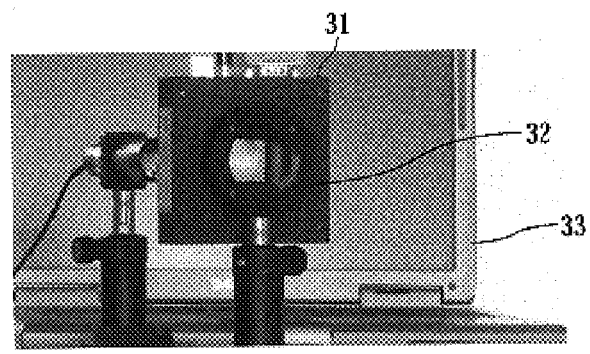
FIG. 3(b) is an illustration of a spatial light.
Figure 7:
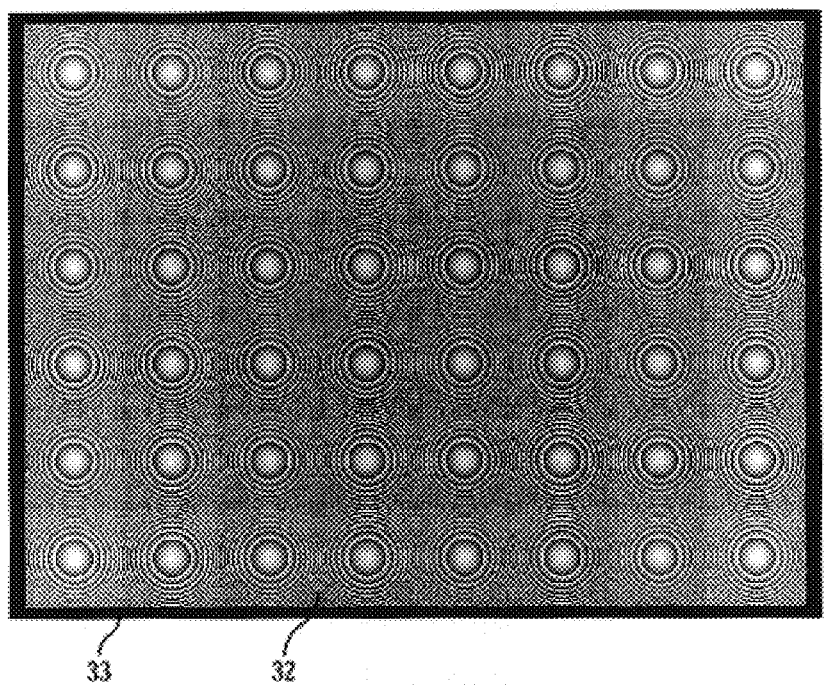
FIG. 7 is an illustration of an array of virtual lenses.

As shown in FIG. 3(b) and FIG. 7, an alternate to the physical microlens array 18, a Spatial Light Modulator (SLM) 31 may be used to display a virtual microlens array 32 on a display 33 as desired by the specific application. This provides more flexibility in the number of points which can be analyzed during the strain measurements, the sensitivity, strain range and accuracy of the system. The SLM system could be Liquid Crystal displays (LCD), a liquid crystal on silicon (LCOS), or a digital micromirror device (DMD). These devices modulate light spatially in amplitude and phase, so they act as a dynamic optical element. The microlens array function to be displayed can be taken from optical design software directly and transferred to the SLM device via a computer interface. Implementation may be by addressing using VGA or DVI signals directly from a computer graphics card.

Figure 6:
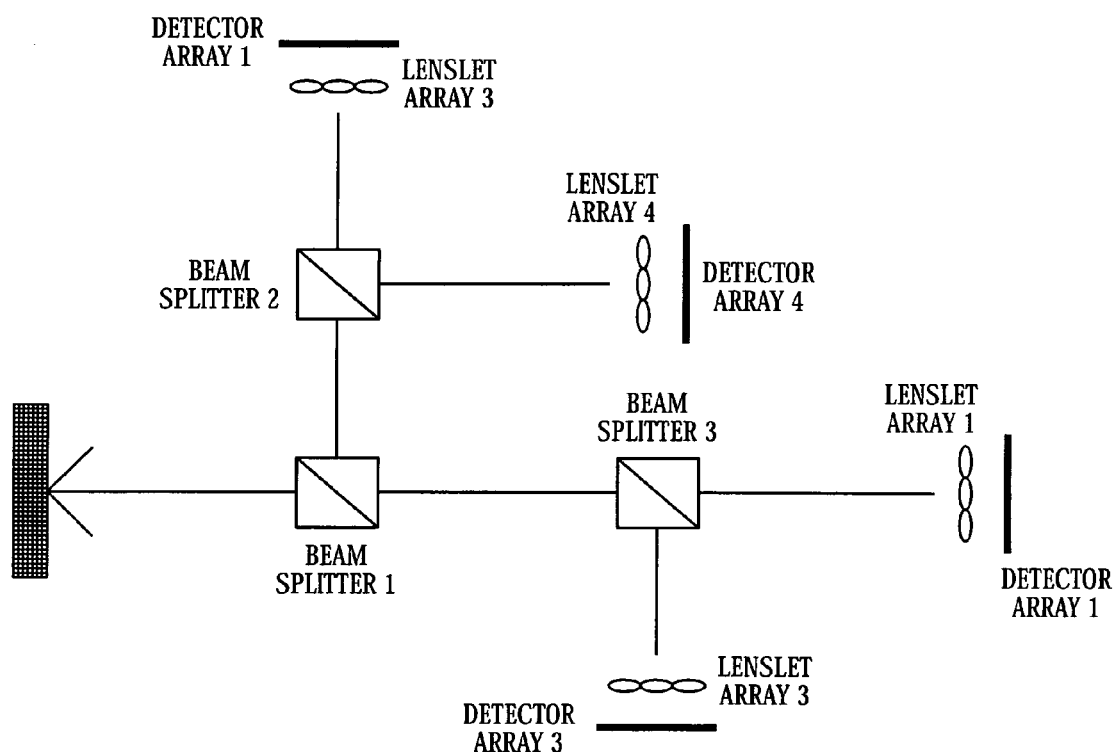
FIG. 6 is an illustration of a system to measure strain at different ranges/sensitivities using a plurality of beam splitters and a plurality of microlens and detector arrays.

As shown in FIG. 6, to measure strain at different ranges and/or sensitivities, it is also possible to use multiple beam splitters 28 and with sets of different microlens arrays 18 and detectors 20. The different microlens arrays 18 may be of the same sensitivity, or may be of different sensitivities.

Figure 8:
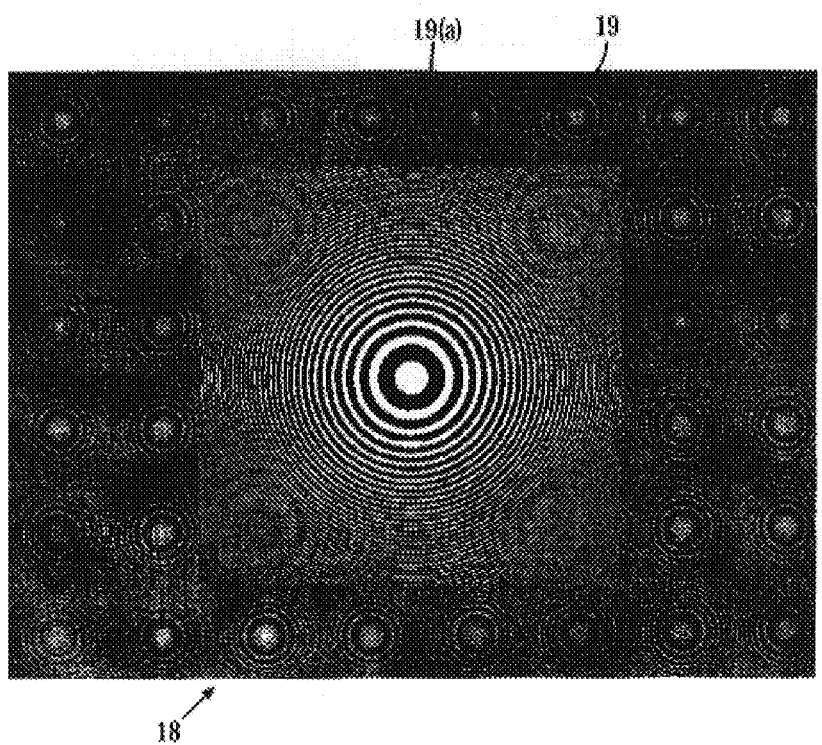
FIG. 8 is an illustration of an array of virtual lenses, the lenses being of different sizes.

As shown in FIG. 8, it may be advantageous to use different size lenses 19 at different regions in the lens array 18 to improve sensitivity in regions of high strain gradient and increase speed in regions where strain is varying slowly by having fewer lenses 19. As each lens 19 generates data, having one larger lens 19(a) in a region where sensitivity is not required reduces the data to be processed.

Whilst there has been described in the foregoing description preferred embodiments of the present invention, it will be understood by those skilled in the technology concerned that many variations or modifications in details of design or construction may be made without departing from the present invention.

The invention claimed is:

1. A moire interferometric strain sensor for detecting strain on a specimen, a diffraction grating being on the specimen, the strain sensor comprising:
   (a) an array of a plurality of microlenses for receiving at least one diffracted beam of at least one incident beam upon the diffraction grating on the specimen; and
   (b) a detector array at a focal plane of the array of a plurality of microlenses;
   wherein the array of a plurality of microlenses is a virtual microlens array on a display.

2. A strain sensor as claimed in claim 1, wherein the grating is a high frequency grating attached to a surface of the specimen.

3. A strain sensor as claimed in claim 1, wherein the at least one incident beam comprises two symmetrical beams each incident on the specimen at an angle, the two symmetrical beams being co-incident in a reference state.

4. A strain sensor as claimed in claim 3, wherein each of the symmetrical beams is a collimated beam.

5. A strain sensor as claimed in claim 3, wherein the angle is determined by the frequency of the diffraction grating, which is a high frequency grating.

6. A strain sensor as claimed in claim 1, wherein the array of a plurality of microlenses is selected from the group consisting of: close packed, and spaced apart.

7. A strain sensor as claimed in claim 1, wherein each of the plurality of detectors is selected from the group consisting of: a charge coupled device, and a complimentary metal oxide device.

8. A strain sensor as claimed in claim 1, wherein the microlens array comprises a plurality of microlenses all being substantially identical.

9. A strain sensor as claimed in claim 1 further comprising at least one further array of microlenses for receiving the at least one diffracted beam of the at least one incident beam upon the diffraction grating on the specimen; and at least one further detector array at a focal plane of the at least one further array of microlenses, the at least one further array of microlenses being of a same sensitivity relative to that of the array of microlenses.

10. A strain sensor as claimed in claim 1, wherein the virtual microlens array is generated by a spatial light modulator.

11. A strain sensor as claimed in claim 10, wherein the spatial light modulator is selected from the group consisting of: a liquid crystal display, a liquid crystal on silicon, and a digital micromirror device.

12. A strain sensor as claimed in claim 1, wherein the microlens array comprises a plurality of microlenses of different sizes.

13. A strain sensor as claimed in claim 1, the strain sensor further comprising at least one light source for directing at least two light beams on the diffraction grating, the at least two light beams being able to illuminate at least a major portion of the diffraction grating without movement of the at least two light beams.

14. A strain sensor as claimed in claim 13, wherein the at least two light beams are coincident on the diffraction grating when the diffraction grating is in a reference state.

15. A strain sensor as claimed in claim 13, wherein the at least two light beams are symmetrical about a line perpendicular to the specimen.

16. A strain sensor as claimed in claim 13, where the at least two light beams are of the same frequency, the frequency being determined by the diffraction grating frequency.

17. A strain sensor as claimed in claim 13, wherein there is a single light source, the at least two beams being from the single light source.

18. A strain sensor as claimed in claim 13, wherein the at least two beams are collimated beams.

19. A strain sensor as claimed in claim 1 further comprising at least one further array of microlenses for receiving the at least one diffracted beam of the at least one incident beam upon the diffraction grating on the specimen; and at least one further detector array at a focal plane of the at least one further array of microlenses, the at least one further array of microlenses being of a different sensitivity relative to that of the array of microlenses.

20. A method for detecting a strain on a specimen, the method comprising:
   placing a high frequency diffraction grating on the specimen;
   providing at least one incident beam on the specimen at the diffraction grating to cause at least one diffracted beam;
   using an array of a plurality of microlenses to receive the at least one diffracted beam;
   detecting the at least one diffracted beam at a detector array at a focal plane of an array of a plurality of microlenses, the diffracted beam forming a plurality of spots on the detector array; and
   measuring separation of spot centroids of the plurality of spots to determine strain on the specimen.

21. A method as claimed in claim 20, wherein the high frequency diffraction grating is attached to a surface of the specimen.

22. A method as claimed in claim 20, wherein the at least one incident beam comprises two symmetrical beams each incident on the specimen at an angle.

23. A method as claimed in claim 22, wherein each of the symmetrical beams is a collimated beam.

24. A method as claimed in claim 22, wherein the angle is determined by the frequency of the high frequency diffraction grating.

25. A method as claimed in claim 20, wherein the array of a plurality of microlenses is selected from the group consisting of: close packed, and spaced apart.

26. A method as claimed in claim 20, wherein each of the plurality of detectors is selected from the group consisting of: a charge coupled device, and a complimentary metal oxide device.

27. A method as claimed in claim 20, wherein the microlens array comprises a plurality of microlenses of different sizes.

28. A method as claimed in claim 20, wherein the microlens array comprises a plurality of microlenses all being substantially identical.

29. A method as claimed in claim 20 further comprising using at least one further array of microlenses to receive the at least one diffracted beam; and detecting the at least one diffracted beam at at least one further detector array at a focal plane of the at least one further array of microlenses, the at least one further array of microlenses being of a same sensitivity relative to that of the array of microlenses.

30. A method as claimed in claim 20, wherein the microlens array is a virtual microlens array.

31. A method as claimed in claim 30, wherein a spatial light modulator is used to produce the virtual microlens array.

32. A method as claimed in claim 31, wherein the spatial light modulator is selected from the group consisting of: a liquid crystal display, a liquid crystal on silicon, and a digital micro-mirror device.

33. A method as claimed in claim 20, the method further comprising placing a high frequency diffraction grating on a surface of the specimen; providing at least one light source for directing at least two light beams on the diffraction grating, the at least two light beams illuminating at least a major portion of the diffraction grating without movement of the at least two light beams.

34. A method as claimed in claim 33, wherein the at least two light beams are coincident on the diffraction grating when the diffraction grating is in a reference state.

35. A method as claimed in claim 33, wherein the at least two light beams are symmetrical about a line perpendicular to the specimen.

36. A method as claimed in claim 33, where the at least two light beams are of the same frequency, the frequency being determined by the diffraction grating frequency.

37. A method as claimed in claim 33, wherein there is a single light source, the at least two beams being from the single light source.

38. A method as claimed in claim 33, wherein the at least two beams are collimated beams.

39. A method as claimed in claim 20 further comprising using at least one further array of microlenses to receive the at least one diffracted beam; and detecting the at least one diffracted beam at at least one further detector array at a focal plane of the at least one further array of microlenses, the at least one further array of microlenses being of a different sensitivity relative to that of the array of microlenses.

* * * * *